(12) United States Patent
Ward (10) Patent No.: US 7,970,449 B2
(45) Date of Patent: *Jun. 28, 2011

(54) METHOD AND APPARATUS FOR BACKGROUND CURRENT ARRANGEMENTS FOR A BIOSENSOR

(75) Inventor: W. Kenneth Ward, Portland, OR (US)

(73) Assignee: Isense Corporation, Wilsonville, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/758,638

(22) Filed: Apr. 12, 2010

(65) Prior Publication Data

US 2010/0198031 A1 Aug. 5, 2010

Related U.S. Application Data

(63) Continuation of application No. 11/559,521, filed on Nov. 14, 2006, now Pat. No. 7,729,737.

(60) Provisional application No. 60/739,147, filed on Nov. 22, 2005.

(51) Int. Cl.
*A61B 5/04* (2006.01)

(52) U.S. Cl. ........ 600/347; 600/348; 600/316; 600/317; 600/365

(58) Field of Classification Search .......... 600/347–348, 600/316–317, 322, 365
See application file for complete search history.

(56) References Cited

U.S. PATENT DOCUMENTS

| | | | | |
|---|---|---|---|---|
| 6,233,471 | B1 * | 5/2001 | Berner et al. | 600/345 |
| 6,736,777 | B2 * | 5/2004 | Kim et al. | 600/365 |
| 6,802,957 | B2 * | 10/2004 | Jung et al. | 205/777.5 |
| 6,885,883 | B2 * | 4/2005 | Parris et al. | 600/347 |
| 2003/0235817 | A1 * | 12/2003 | Bartkowiak et al. | 435/5 |

* cited by examiner

*Primary Examiner* — Charles A Marmor, II
*Assistant Examiner* — Michael D'Angelo
(74) *Attorney, Agent, or Firm* — Schwabe, Williamson & Wyatt, P.C.

(57) ABSTRACT

Embodiments of the present invention provide for raising a background current setting for a biosensor above the actual (measured) background current present (i.e., overestimating the background current), particularly in the hypoglycemic range, to improve sensor accuracy and decrease the chance of glucose value overestimation by the sensor.

19 Claims, 6 Drawing Sheets

FIG. 1

| ENTIRE GLUCOSE RANGE | | | | | | | | |
|---|---|---|---|---|---|---|---|---|
| # | Background Current (nA) | A | B | A+B | C | D | E | MARD | Comments |
| 1 | 0 | 69.3% | 27.1% | 96.3% | 0.7% | 3.0% | 0.0% | 17.7% | First 3 settings lead to good MARD and good EGA. 4th setting has higher MARD. |
| 2 | 0.8 | 69.1% | 27.9% | 96.9% | 1.0% | 2.1% | 0.0% | 17.5% | |
| 3 | 1.5 | 68.3% | 29.1% | 97.4% | 1.2% | 1.4% | 0.0% | 18.3% | |
| 4 | 2.2 | 64.8% | 33.2% | 98.0% | 1.1% | 0.9% | 0.0% | 20.4% | |

FIG. 2

| HYPOGLYCEMIC RANGE | | | | | | | | |
|---|---|---|---|---|---|---|---|---|
| # | Background Current (nA) | A | B | A+B | C | D | E | MARD | Comments |
| 1 | 0 | 60.9% | 13.0% | 73.9% | 0.0% | 26.1% | 0.0% | 29% | Third setting has excellent EGA and excellent MARD. Note minimal D range values for 3rd and 4th settings. |
| 2 | 0.8 | 70.9% | 12.8% | 83.7% | 0.0% | 16.3% | 0.0% | 22% | |
| 3 | 1.5 | 83.5% | 10.1% | 93.7% | 0.0% | 6.3% | 0.0% | 20% | |
| 4 | 2.2 | 84.6% | 13.8% | 98.5% | 0.0% | 1.5% | 0.0% | 26% | |

Variable Background Current

| MARD | Range | | Count | Percentage | Background Current |
|---|---|---|---|---|---|
| 19.60 | 0-75 | A | 66 | 83.54% | 1.50 |
| | | B | 8 | 10.13% | |
| | | A+B | 74 | 93.67% | |
| | | C | 0 | 0.00% | |
| | | D | 5 | 6.33% | |
| | | E | 0 | 0.00% | |
| | | Total | 79 | 100.00% | |
| 17.90 | 76-150 | A | 312 | 66.95% | 0.80 |
| | | B | 154 | 33.05% | |
| | | A+B | 466 | 100.00% | |
| | | C | 0 | 0.00% | |
| | | D | 0 | 0.00% | |
| | | E | 0 | 0.00% | |
| | | Total | 466 | 100.00% | |
| 17.00 | 151-225 | A | 224 | 69.14% | 0.80 |
| | | B | 93 | 28.70% | |
| | | A+B | 317 | 97.84% | |
| | | C | 7 | 2.16% | |
| | | D | 0 | 0.00% | |
| | | E | 0 | 0.00% | |
| | | Total | 324 | 100.00% | |
| 14.20 | 226-300 | A | 89 | 74.79% | 0.80 |
| | | B | 21 | 17.65% | |
| | | A+B | 110 | 92.44% | |
| | | C | 3 | 2.52% | |
| | | D | 6 | 5.04% | |
| | | E | 0 | 0.00% | |
| | | Total | 119 | 100.00% | |
| 14.20 | >300 | A | 8 | 80.00% | 0.80 |
| | | B | 1 | 10.00% | |
| | | A+B | 9 | 90.00% | |
| | | C | 0 | 0.00% | |
| | | D | 1 | 10.00% | |
| | | E | 0 | 0.00% | |
| | | Total | 10 | 100.00% | |
| 17.26 | ALL RANGES | A | 699 | 70.0% | ALL RANGES |
| | | B | 277 | 27.8% | |
| | | A+B | 976 | 97.8% | |
| | | C | 10 | 1.0% | |
| | | D | 12 | 1.2% | |
| | | E | 0 | 0.0% | |
| | | Total | 998 | 100.0% | |

Background Current fixed at 0.8

| MARD | Range | | Count | Percentage |
|---|---|---|---|---|
| 21.90 | 0-75 | A | 61 | 70.93% |
| | | B | 11 | 12.79% |
| | | A+B | 72 | 83.72% |
| | | C | 0 | 0.00% |
| | | D | 14 | 16.28% |
| | | E | 0 | 0.00% |
| | | Total | 86 | 100.00% |
| 17.90 | 76-150 | A | 312 | 66.95% |
| | | B | 154 | 33.05% |
| | | A+B | 466 | 100.00% |
| | | C | 0 | 0.00% |
| | | D | 0 | 0.00% |
| | | E | 0 | 0.00% |
| | | Total | 466 | 100.00% |
| 17.00 | 151-225 | A | 224 | 69.14% |
| | | B | 93 | 28.70% |
| | | A+B | 317 | 97.84% |
| | | C | 7 | 2.16% |
| | | D | 0 | 0.00% |
| | | E | 0 | 0.00% |
| | | Total | 324 | 100.00% |
| 14.20 | 226-300 | A | 89 | 74.79% |
| | | B | 21 | 17.65% |
| | | A+B | 110 | 92.44% |
| | | C | 3 | 2.52% |
| | | D | 6 | 5.04% |
| | | E | 0 | 0.00% |
| | | Total | 119 | 100.00% |
| 14.20 | >300 | A | 8 | 80.00% |
| | | B | 1 | 10.00% |
| | | A+B | 9 | 90.00% |
| | | C | 0 | 0.00% |
| | | D | 1 | 10.00% |
| | | E | 0 | 0.00% |
| | | Total | 10 | 100.00% |
| 17.49 | ALL RANGES | A | 694 | 69.05% |
| | | B | 280 | 27.86% |
| | | A+B | 974 | 96.92% |
| | | C | 10 | 1.00% |
| | | D | 21 | 2.09% |
| | | E | 0 | 0.00% |
| | | Total | 1005 | 100.00% |

Background Current fixed at 1.5

| MARD | Range | | Count | Percentage |
|---|---|---|---|---|
| 19.60 | 0-75 | A | 66 | 83.54% |
| | | B | 8 | 10.13% |
| | | A+B | 74 | 93.67% |
| | | C | 0 | 0.00% |
| | | D | 5 | 6.33% |
| | | E | 0 | 0.00% |
| | | Total | 79 | 100.00% |
| 19.52 | 76-150 | A | 261 | 63.35% |
| | | B | 150 | 36.41% |
| | | A+B | 411 | 99.76% |
| | | C | 1 | 0.24% |
| | | D | 0 | 0.00% |
| | | E | 0 | 0.00% |
| | | Total | 412 | 100.00% |
| 17.40 | 151-225 | A | 199 | 70.07% |
| | | B | 78 | 27.46% |
| | | A+B | 277 | 97.54% |
| | | C | 7 | 2.46% |
| | | D | 0 | 0.00% |
| | | E | 0 | 0.00% |
| | | Total | 284 | 100.00% |
| 15.27 | 226-300 | A | 75 | 73.53% |
| | | B | 18 | 17.65% |
| | | A+B | 93 | 91.18% |
| | | C | 3 | 2.94% |
| | | D | 6 | 5.88% |
| | | E | 0 | 0.00% |
| | | Total | 102 | 100.00% |
| 17.18 | >300 | A | 5 | 50.00% |
| | | B | 4 | 40.00% |
| | | A+B | 9 | 90.00% |
| | | C | 0 | 0.00% |
| | | D | 1 | 10.00% |
| | | E | 0 | 0.00% |
| | | Total | 10 | 100.00% |
| 18.33 | ALL RANGES | A | 606 | 68.32% |
| | | B | 258 | 29.09% |
| | | A+B | 864 | 97.41% |
| | | C | 11 | 1.24% |
| | | D | 12 | 1.35% |
| | | E | 0 | 0.00% |
| | | Total | 887 | 100.00% |

FIG. 5

- Now, when the glucose really is 70, an "unknown" sensor value of 8.8 nA is measured (red).
- Using a background of 2, this reading calculates an estimated glucose of 68 mg/dl.
- That is, Estimated glucose = net nA/sensitivity = 6.8/0.1.
- This data pair is in the A range (actual G = 70, sensor estimated G = 68)

- Now, WHAT IF the background had been zero under the same circumstances?
- the sensitivity during the calibration at 200 mg/dl would have been 22/200 which equals 0.11
- Now, again assume an unknown sensor value of 8.8 nA at a true glucose of 70.
- Estimated glucose = net nA/0.11 = 8.8/0.11 = 80
- So, this data pair is in the D range (actual G = 70, sensor estimated G = 80)

METHOD AND APPARATUS FOR BACKGROUND CURRENT ARRANGEMENTS FOR A BIOSENSOR

CROSS REFERENCE TO RELATED APPLICATIONS

The present application is a continuation of and claims priority to U.S. patent application Ser. No. 11/559,521, filed Nov. 14, 2006, entitled "Method and Apparatus for Background Current Arrangements for a Biosensor," which claims priority to U.S. Provisional Patent Application No. 60/739,147, filed Nov. 22, 2005, entitled "Method and Apparatus for Variable Background Current Arrangement for a Biosensor," the entire disclosures of which are hereby incorporated by reference in their entirety.

TECHNICAL FIELD

Embodiments of the present invention relate to the field of medical devices and, more specifically, to background current arrangements for a biosensor.

BACKGROUND

In an amperometric enzyme sensor, the background current refers to the small amount of current that exists even in the absence of the analyte that is being measured. This value may be measured in sensors that are specially constructed without enzyme, thus being incapable of a response to an analyte such as glucose or lactate. When such sensors (those lacking an enzyme) have been implanted in animals or in humans, an exemplary background current has been typically between about 0.5 and 2 nA (nanoamperes).

In addition, the accuracy of a glucose biosensor in the hypoglycemic range is quite important from a clinical standpoint. For example, if the true capillary blood glucose is really 65 mg/dl (low) and the sensor estimate is 80 mg/dl, this is a serious error, i.e. true hypoglycemia was missed due to a sensor overestimate. Misdiagnosis of hypoglycemia could lead to coma, seizures, automobile accidents, etc.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the accompanying figures.

FIG. 4 is a table illustrating results of Clarke Error Grid Analysis regions and Mean Absolute Relative Difference (MARD) data using a variable background current method (left panel), a fixed background current method of 0.8 nA (middle panel), and a fixed background current of 1.5 nA (right panel);

DETAILED DESCRIPTION OF EMBODIMENTS OF THE INVENTION

In the following detailed description, reference is made to the accompanying drawings which form a part hereof, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the present invention, a phrase in the form "A/B" means A or B. For the purposes of the present invention, a phrase in the form "A and/or B" means "(A), (B), or (A and B)". For the purposes of the present invention, a phrase in the form "at least one of A, B, and C" means "(A), (B), (C), (A and B), (A and C), (B and C), or (A, B and C)". For the purposes of the present invention, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In embodiments of the present invention, it is provided that by raising the background current setting above the actual (measured) background current present (i.e., overestimating the background current), particularly in the hypoglycemic range, the sensor accuracy improves and decreases the chance of glucose value overestimation by the sensor.

Methods in accordance with embodiments of the present invention lead to a degree of underestimation of the glucose value which may be clinically favorable, particularly in the hypoglycemic range. Specifically, this may reduce the incidences of overestimation of glucose values that are truly in the hypoglycemic range. Thus, in an embodiment, a reduction in the number of false negative (inaccurately hypoglycemic) values may be provided. In the hypoglycemic range, the difference may be important and clinically significant, even when the degree of background current change is small.

In an embodiment of the present invention, an algorithm operating in real time may utilize different background current values for different glucose ranges.

In an exemplary embodiment, a background current value of, for example, approximately 1.3-1.7 nA may be well-suited for a hypoglycemic range (for example 90 mg/dl and below, or 70 mg/dl and below) and a value of, for example, approximately 0.6-1.0 nA may be well-suited for the remaining ranges (above 70 mg/dl, or above 90 mg/dl). In embodiments, other threshold values may be used as well.

While the above-mentioned background current values may work well for one or more particular sensors, for other different sensors it may be necessary to use different values. In other words, in an embodiment of the present invention, for a sensor that allows more interfering agents to reach a working electrode, the background currents may be higher at all glucose levels—but embodiments of the present invention are still applicable. That is, the use of a higher background current for lower glucose values leads to a clinical improvement by reducing the likelihood of overestimating values in the lower glucose range.

Thus, in an embodiment, there is provided a method comprising determining an initial background current value of an analyte sensor; determining for the analyte sensor in use an initial analyte sensor output value using the initial background current value; adjusting the initial background current value by a factor based on the determined initial analyte sensor output value to form an adjusted background current value; and forming an adjusted analyte sensor output value using the adjusted background current value.

In an embodiment of the present invention, a factor may be a multiplication factor, for example less than 3, or less than 2, an absolute/numeric value increase or decrease (for example −3 mg/dl), or it may be an increase or decrease along a predetermined scale of values.

In an embodiment, a series of background current values may be predefined, such as 0, 0.8, 1.5, 2.2, 3.0 nA, etc. When a determination is made as to the measured/existing background current, in accordance with an embodiment of the present invention, the background current utilized for the ultimate determination of estimated glucose value may be the next highest background current value in the predefined list. In an alternative embodiment, the next highest (or second highest, etc., as desired) background current value may be substituted for the measured value only when the initial estimated glucose value is less than a predetermined threshold, such as 70 mg/dl or 90 mg/dl.

In an embodiment, when an estimated glucose value is in a predefined range or below a predefined value, the measured background current may be adjusted by a certain percentage or a certain value of nanoamps depending on the particular initial estimated glucose value. In an embodiment, the adjustment in the background current may be inversely proportional to the average rate at which the glucose level has been falling over a predetermined amount of time. For example, if over the past 10 minutes the estimated glucose value of an individual has been falling at 1 mg/dl/minute, then the background current may be adjusted by, for example, 0.1 nA per minute measured. Thus, over a 10 minute period having an average rate of glucose decline of 1 mg/dl/minute, a measured background current of 1.0 nA may be modified to form an adjusted background current value of 2.0 nA. This is simply an example of the concept and thus the particular rates, thresholds, and/or modifications may be adjusted or set as desired in accordance with the teachings of embodiments of the present invention.

In a simplified embodiment, a fixed background current may be used and the resultant initial glucose values determined may be adjusted by a factor (such as a reducing factor). Such a factor may be an increase or decrease in the initial glucose value by a percentage of the initial value or a fixed amount. In another embodiment, the factor may change depending on the initial glucose value. For example, if the initial glucose value is below 90 mg/dl the value may be adjusted by reducing the value, for example, by 5%-10% or less than approximately 15% or 10%, or by a fixed amount of, for example, 5 mg/dl. In addition, in an embodiment, if the initial glucose value is above 90 mg/dl the value may not be adjusted. A reducing factor of 5%, for example, means that a glucose value is reduced by 5% such that an initial glucose value of 80 mg/dl would provide an adjusted glucose value of 76 mg/dl after applying the factor. Such embodiments ensures that values in or approaching hypoglycemia are adjusted toward a hypoglycemic reading to attempt to ensure that a true hypoglycemic condition is not missed. Embodiments of the present invention may cause a resultant decrease in sensitivity and/or increase the number of false alarms for hypoglycemia; however, the benefits of ensuring a true hypoglycemic condition is not missed outweighs the concerns over potential loss of sensitivity and/or an increase in false alarms.

Thus, in an embodiment, there is provided a method for obtaining an analyte value of a sample using an analyte sensor, comprising determining a fixed background current value to be used for the analyte sensor; bringing the analyte sensor into contact with the sample to form an initial analyte sensor current value; subtracting the fixed background current value from the initial analyte sensor current value to form a net analyte sensor current value; dividing the net analyte sensor current value by a sensitivity value of the analyte sensor to form an estimated glucose value; and displaying the estimated glucose value if the estimated glucose value is above a predefined threshold, and applying a reducing factor if the estimated glucose value is at or below the predefined threshold to form an adjusted glucose value and then displaying the adjusted glucose value.

In an embodiment using a one-point calibration, the background current may be subtracted from the sensor output (in units of nA). The value (net sensor output) may then be divided by the capillary glucose level taken at the time of calibration, yielding a sensitivity value. In an embodiment, for calculation (estimation) of the glucose concentration based on a sensor reading, the following calculation may be made: the background current is subtracted from the total sensor output, and the value is then divided by the sensitivity, yielding an estimated glucose value. Thus, adjusting the background current clearly has an impact on the established sensitivity of the sensor, and thus has an impact on the estimated glucose value.

In embodiments of the present invention, a multi-point system of calibration may be used instead of a one-point system. In a multi-point system, the current one-point sensor value (estimated glucose value) and capillary blood glucose may be used and, in addition, a time-weighted series of previous sensor values and capillary blood glucose values may be used. For example, in a multi-point system, the present value may be provided a weighting of 80% and all the previous values may be provided a total weight of 20% (with values more remote in time having the least weight). In such a manner, some or all of the previous calibration values (over many days) may be used in a multi-point calibration system.

Thus, in an embodiment there is provided a method comprising subtracting a first background current value of an analyte sensor from a first analyte sensor output value to form a first net analyte sensor output value; obtaining a capillary glucose level of an individual; dividing the first net analyte sensor output value by the capillary glucose level to form a sensitivity value; determining a second background current value of the analyte sensor; determining for the analyte sensor a second analyte sensor output value using the second background current value; adjusting the second background current value by a factor based on the determined second analyte sensor output value to form a third background current value; subtracting the third background current value from the second analyte sensor output value to form a second net analyte sensor output value; and dividing the second net analyte sensor output value by the sensitivity value to form an estimated glucose value.

In addition, embodiments of the present invention may use various processing and/or computing devices to carry out the desired methods and calculations. In addition, the data derived in accordance with various embodiments of the present invention may be displayed on a variety of devices, and may be transmitted in a variety of ways. Thus, in an embodiment there is provided an apparatus comprising a storage medium having stored therein a plurality of programming instructions designed to enable the apparatus, when the programming instructions are executed, to determine an initial background current value of an analyte sensor, determine for the analyte sensor in use an initial analyte sensor output value using the initial background current value, adjust the initial background current value by a factor based on the determined initial analyte sensor output value to form an adjusted background current value, and form an adjusted analyte sensor output value using the adjusted background current value; and a processor coupled to the storage medium to execute the plurality of programming instructions.

Other data algorithms that assist in maximizing accuracy in accordance with embodiments of the present invention include biological filters. Specifically, an understanding of normal physiology reveals that there are limits on the rates at which glucose concentration in the human body may rise or fall. Factors that govern the rate of glucose rise include the rate of absorption of carbohydrate from the gut and the rate at which the liver may convert glycogen into glucose during periods of fasting. The rate of glucose decline depends on uptake of glucose into muscle and fat cells, the prevailing insulin concentration, insulin sensitivity, and degree of physical exertion. One may make calculations that are able to model these biologic attributes and thus may separate artifact (e.g. due to movement) from true excursions of glucose concentration.

Another important data analysis algorithm in accordance with embodiments of the present invention is that of dislodgement detection. Specifically, a wire sensor may become partially or fully dislodged due to inadequate contact strength of the module adhesive with the skin. There are techniques that recognize patterns typical of dislodged or partially-dislodged sensors. If movement error is mild, display of the data may be temporarily suspended. If error persists, the patient may be asked to insert a new sensor.

In an exemplary embodiment of the present invention, data from 15 subjects with type 1 diabetes are used, each of whom wore an amperometric wire sensor subcutaneously for 5 consecutive days. In addition to wearing the subcutaneous sensor, these subjects evaluated the accuracy of the sensors by measuring fingerstick capillary blood glucose 17 times per day. In this exemplary embodiment, accuracy was evaluated using the following background current values: 0, 0.8, 1.5, and 2.2 nA (see FIG. 1). Some tests were performed with background current values higher than 2.2 nA (data not shown), but those results led to high values of Mean Absolute Relative Difference (MARD) that were outside of the reasonable range.

Figure 1:
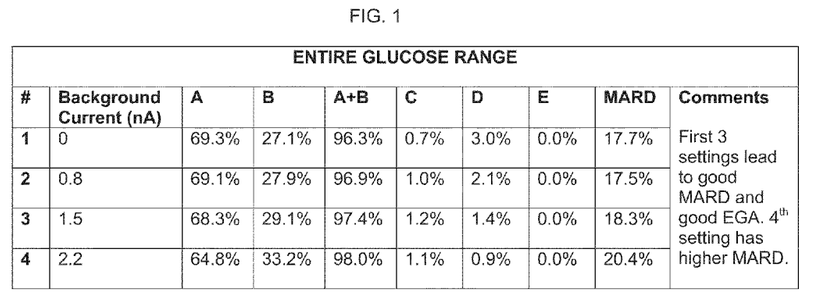
FIG. 1 is a table illustrating the results of using different background current values for a sensor operating in a glucose range of 40-400 mg/dl and the corresponding percentage of data pairs for each Clarke Error Grid Analysis region in accordance with various embodiments of the present invention.

In accordance with an embodiment of the present invention, a tabular summary of results of using different background current values (for the glucose range of 40-400 mg/dl), showing the percentage of data pairs for each Clarke Error Grid Analysis (EGA) region is displayed in FIG. 1. Note that there is some improvement (reduction) in the D range percentage as the background current is raised, which represents an improvement. However, when a background current of 2.2 nA is used, the MARD becomes somewhat elevated, over 20%, but still with a reduction in the D range percentage.

Figure 2:
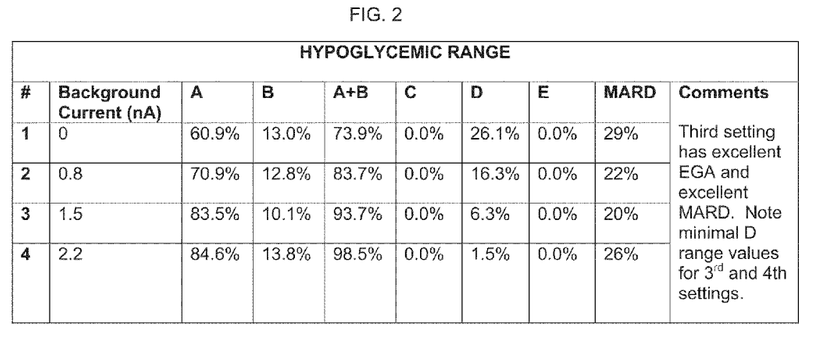
FIG. 2 is a table illustrating the results of using different background current values for a sensor operating in a hypoglycemic glucose range (70 mg/dl and below) and the corresponding percentage of data pairs for each Clarke Error Grid Analysis region in accordance with various embodiments of the present invention.

In addition, the same background current values were used to examine sensor data accuracy specifically in the hypoglycemic range according to an embodiment of the present invention. These accuracy data are shown in FIG. 2. Note that as the background current is raised from 0.8 to 1.5 nA, the accuracy of error grid data and the MARD data improves substantially. Note specifically that the percentage of D values declines markedly, from 26.1% with a background current of 0.0 nA, down to 1.5% with a background current of 2.2 nA. Also note that MARD improves as the background current is raised from 0.0 to 1.5 nA, then it increases again as the background current is raised further to 2.2 nA.

In an embodiment of the present invention, in the hypoglycemic range, a suitable background current value to use may be a value of approximately 1.5 nA. This value leads to an excellent error grid analysis and also an excellent MARD.

The foregoing data demonstrate that using a background current of approximately 1.5 nA works well in the hypoglycemic range. However, in an embodiment of the present invention, an examination of an overall glucose range may indicate that the MARD is best (lowest) when a different background current is utilized, such as 0.8 nA. Thus, an embodiment of the present invention provides for use of different background current values for different glucose ranges.

In an embodiment of the present invention, data was reanalyzed using 1.5 nA as the exemplary background current for the glucose range of 75 mg/dl and below and 0.8 nA for all other ranges. The Error Grid plot of FIG. 3 was generated using such an arrangement.

Figure 3:
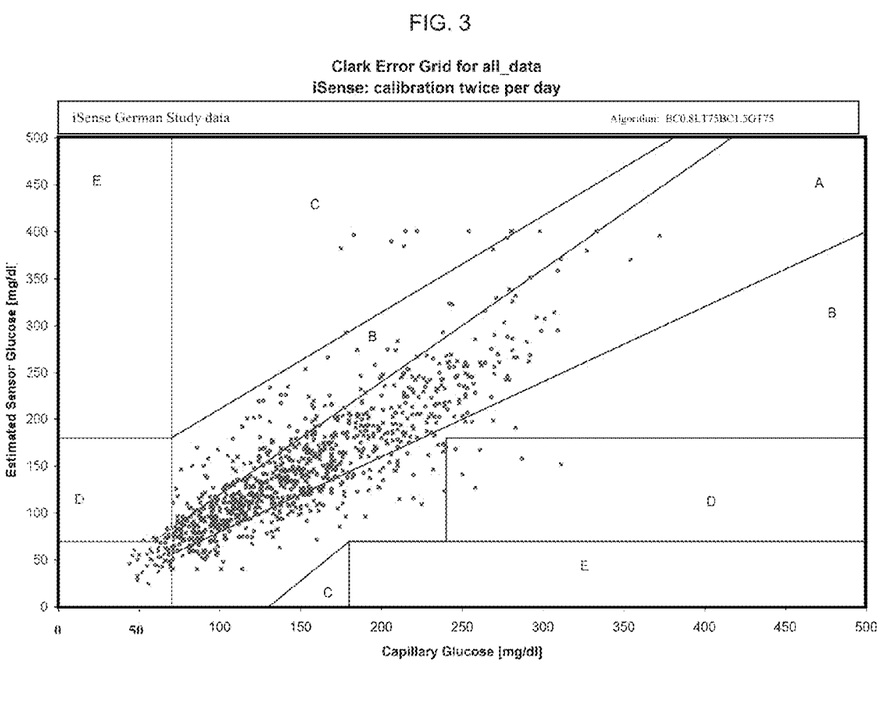
FIG. 3 is an Error Grid Plot of data resulting from a background current of 1.5 nA for a sensor operating in a glucose range of 75 mg/dl and below and a background current of 0.8 nA for glucose values over 75 mg/dl in accordance with various embodiments of the present invention.

In the region below a glucose level of 75 mg/dl, only a few values are in the upper D range, and those values are close to the boundary between the D region and the A region.

In accordance with embodiments of the present invention, FIG. 4 provides results of Error Grid regions and MARD data using a variable background current method (left panel), a fixed background current of 0.8 nA (middle panel) and a fixed background current of 1.5 nA (right panel).

In an embodiment of the present invention as shown in FIG. 4, the variable background current method yields the greatest overall accuracy. For example, such a method may comprise establishing an approximation or estimate of the glucose value, using a fixed background current between two other selected background currents that may be used—e.g. in the example of FIG. 4, a background current of 1 nA (between 0.8 and 1.5 nA) was used to arrive at an estimation. Then, for example, in an embodiment, a background current such as 1.5 nA may be used for the instances with initial glucose estimates of 75 mg/dl or less and a background current such as 0.8 nA for the instances with initial glucose estimates over 75 mg/dl. In embodiments, each estimated value may then be recalculated using the new background current values and the accuracy may be measured.

Using a variable background current method, the percentage of A+B values is highest (97.8%), the percentage of D values is lowest (1.0%) and the MARD is the lowest (17.26%). In the hypoglycemic range, the data for the variable background current method is better than the data where background current was fixed at 0.8 nA.

To apply different background current values to different glucose ranges, even in real time, a provisional background current level (such as 1 nA) may be used to arrive at a provisional initial glucose estimate (which is not shown to the user). For example, this initial estimate may be, for example, 200 mg/dl. This identifies the range, at which point, the algorithm may calculate a final estimate using a background current of, for example, 0.8 nA. If the provisional estimate yields a value in the hypoglycemic range (for example below a criterion somewhere in the range of 65-80 mg/dl), then a background current value of, for example, 1.5 nA may be used instead to calculate the final estimate that is shown to the user.

In embodiments of the present invention, raising the background current may lead to reduction of overestimates (estimating a glucose value higher than it should be reported) in the hypoglycemic range. The following figures illustrate exemplary results.

Figure 5:
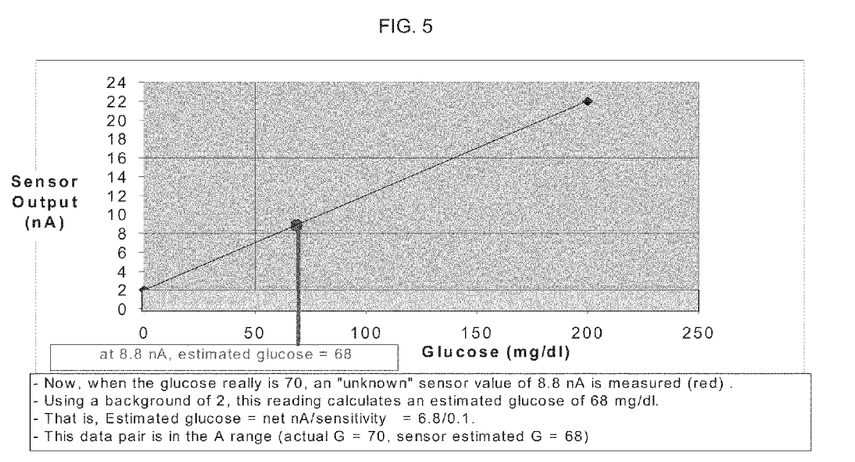
FIG. 5 illustrates an exemplary data plot of sensor output versus glucose value for a sensor background current of 2.0 nA showing an actual glucose value of 70 mg/dl and an estimated glucose value of 68 mg/dl.
Figure 6:
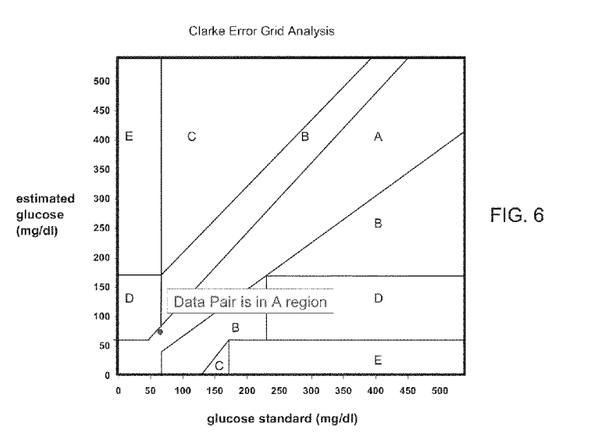
FIG. 6 illustrates the plot of the data of FIG. 5 on the Clarke Error Grid.

In an embodiment of the present invention as shown in FIG. 5, (actual glucose=70 mg/dl and estimated glucose=68 mg/dl), the data pair falls into the error grid region A, as shown in the Error Grid plot of FIG. 6.

Figure 7:
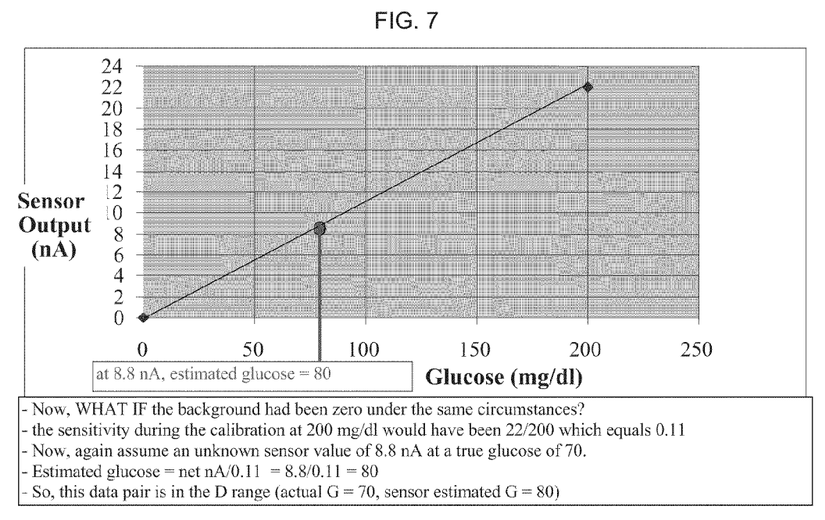
FIG. 7 illustrates an exemplary data plot of sensor output versus glucose value for a sensor background current of 0.0 nA showing an actual glucose value of 70 mg/dl and an estimated glucose value of 80 mg/dl.
Figure 8:
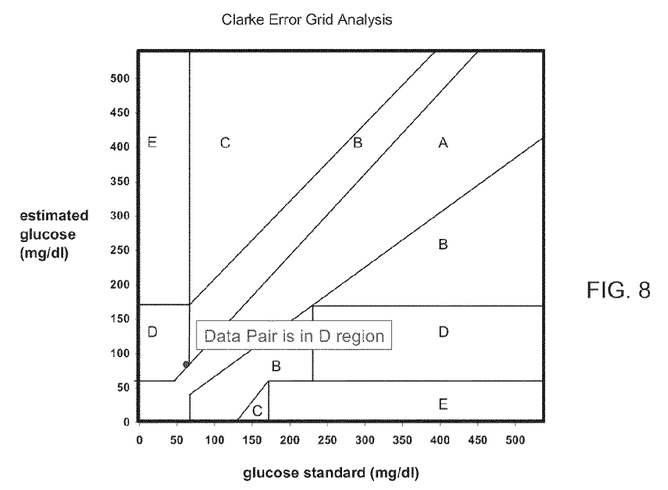
FIG. 8 illustrates the plot of the data of FIG. 7 on the Clarke Error Grid.

In an embodiment of the present invention as shown in FIG. 7, the calibration scheme when the background current is 0.0 nA is illustrated. The data pair (actual glucose of 70 mg/dl, estimated glucose of 80 mg/dl), now falls into the upper D region. The Error Grid plot of FIG. 8 shows that the estimated glucose value falls in the D region.

Figure 9:
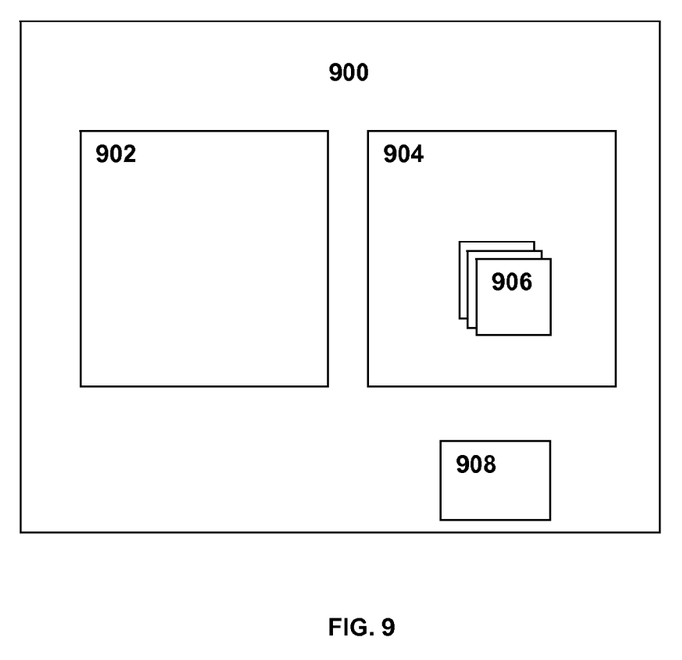
FIG. 9 illustrates an exemplary computing device in accordance with various embodiments.

FIG. 9 illustrates an exemplary computing device 900 configured to carry out various methods and calculations as described in embodiments herein. Computing device 900 includes a processor 902 and a storage medium 904 having a plurality of programming instructions 906. Computing device 900 is also associated with display device 908, which may be integral with or coupled to computing device 900.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method for forming an adjusted analyte sensor value, comprising:
    determining by a computing device for an analyte sensor an initial analyte sensor value using an initial background current value;
    adjusting by the computing device the initial background current value by a factor based on the determined initial analyte sensor value to form an adjusted background current value; and
    forming by the computing device an adjusted analyte sensor value using the adjusted background current value.

2. The method of claim 1, wherein said factor is a multiplication factor applied to the initial background current value.

3. The method of claim 2, wherein said multiplication factor is less than 3.

4. The method of claim 1, wherein said factor comprises an increase or decrease of the initial background current value to an adjusted background current value selected from a predefined list of acceptable adjusted background current values.

5. The method of claim 4, wherein said predefined list of acceptable adjusted background current values comprises 0, 0.8, 1.5, 2.2, and 3.0 nA.

6. The method of claim 1, wherein the adjusted background current value is greater than the initial background current value.

7. The method of claim 1, wherein said based on the initial analyte sensor value comprises determining by the computing device whether the initial analyte sensor value falls within a predetermined range.

8. The method of claim 7, wherein said predetermined range is 70 mg/dl and below.

9. The method of claim 8, wherein said adjusted background current value is approximately 1.3-1.7 nA.

10. The method of claim 7, wherein said predetermined range is above 70 mg/dl.

11. The method of claim 10, wherein said adjusted background current value is approximately 0.6-1.0 nA.

12. The method of claim 1, further comprising determining by the computing device the initial background current value by providing by a computing device an arbitrary background current level within a range of approximately 0.5 to 2.0 nA.

13. The method of claim 1, wherein said adjusted analyte sensor value is displayed on an associated display device.

14. The method of claim 1, wherein said adjusted background current value is further adjusted in real time as the adjusted analyte sensor value changes.

15. The method of claim 1, wherein said using the initial background current value comprises subtracting by the computing device the initial background current value from a first measured analyte sensor value to form said initial analyte sensor value, and said using the adjusted background current value comprises subtracting by the computing device the adjusted background current value from a second measured analyte sensor value to form said adjusted analyte sensor value.

16. The method of claim 1, wherein said factor is defined as a percentage of the initial background current value.

17. The method of claim 1, further comprising determining a rate at which an analyte level has changed during a time period, and wherein said factor is defined as an amount inversely proportional to the rate.

18. An apparatus comprising:
    a storage medium having stored therein a plurality of programming instructions designed to enable the apparatus, as a result of execution of the programming instructions, to determine for an analyte sensor in use an initial analyte sensor value using an initial background current value, adjust the initial background current value by a factor based on the determined initial analyte sensor value to form an adjusted background current value, and form an adjusted analyte sensor value using the adjusted background current value; and
    a processor coupled to the storage medium to execute the plurality of programming instructions.

19. An article of manufacture including a computer-readable medium having instructions stored thereon that, in response to execution by a computing device, cause the computing device to perform a method comprising:

determining by the computing device for an analyte sensor an initial analyte sensor value using an initial background current value;

adjusting by the computing device the initial background current value by a factor based on the determined initial analyte sensor value to form an adjusted background current value; and forming by the computing device an adjusted analyte sensor value using the adjusted background current value.

* * * * *